(12) United States Patent
Wu et al.

(10) Patent No.: US 9,595,092 B2
(45) Date of Patent: Mar. 14, 2017

(54) METHODS AND SYSTEMS FOR INSPECTION OF COMPOSITE IRREGULARITIES

(71) Applicant: The Boeing Company, Seal Beach, CA (US)

(72) Inventors: Yuan-Jye Wu, Issaquah, WA (US); Hong Tat, Redmond, WA (US); Benjamin E. C. Koltenbah, Federal Way, WA (US); Vicki Wu, Seattle, WA (US)

(73) Assignee: The Boeing Company, Chicago, IL (US)

( * ) Notice: Subject to any disclaimer, the term of this patent is extended or adjusted under 35 U.S.C. 154(b) by 436 days.

(21) Appl. No.: 13/891,688

(22) Filed: May 10, 2013

(65) Prior Publication Data

US 2014/0333758 A1 Nov. 13, 2014

(51) Int. Cl.
| | | |
|---|---|---|
| G06T 7/00 | (2006.01) | |
| G01N 29/06 | (2006.01) | |
| G01N 29/44 | (2006.01) | |
| G01N 21/88 | (2006.01) | |
| G01N 21/95 | (2006.01) | |
| G01N 21/84 | (2006.01) | |

(52) U.S. Cl.
CPC ........... *G06T 7/0004* (2013.01); *G01N 21/88* (2013.01); *G01N 21/8851* (2013.01); *G01N 21/95* (2013.01); *G01N 29/069* (2013.01); *G01N 29/4454* (2013.01); *G01N 2021/8438* (2013.01); *G01N 2021/8472* (2013.01); *G01N 2291/0231* (2013.01); *G01N 2291/0289* (2013.01); *G06T 2207/10132* (2013.01); *G06T 2207/30164* (2013.01)

(58) Field of Classification Search
None
See application file for complete search history.

(56) References Cited

U.S. PATENT DOCUMENTS

| | | | |
|---|---|---|---|
| 4,412,315 A | 10/1983 | Flournoy | |
| 4,461,178 A | 7/1984 | Chamuel | |
| 4,592,237 A * | 6/1986 | Ogura | G01N 29/07 73/602 |
| 4,896,278 A * | 1/1990 | Grove | G01N 29/265 250/559.46 |

(Continued)

OTHER PUBLICATIONS

Miencazkowski, M., et al.; Modeling of Ultrasonic Wave Propagation in Composite Airframe Components; Review of Quantitative Nondestructive Evaluation; 2008; pp. 995-1001; vol. 27; American Institute of Physics.

(Continued)

*Primary Examiner* — Tsung-Yin Tsai
(74) *Attorney, Agent, or Firm* — Armstrong Teasdale LLP (57) ABSTRACT

A method for inspecting a composite structure includes acquiring an image of the composite structure. The composite structure includes at least a first ply and a second ply adjacent the first ply. The method also includes transforming the image into a binary image, and determining a first boundary line between the first ply and the second ply. The method further includes characterizing an irregularity in the composite structure based at least partially on the first boundary line.

9 Claims, 5 Drawing Sheets

(56) References Cited

U.S. PATENT DOCUMENTS

| | | | |
|---|---|---|---|
| 5,341,436 A * | 8/1994 | Scott | G01N 23/043 |
| | | | 382/141 |
| 5,402,235 A * | 3/1995 | Monchalin | G01H 9/002 |
| | | | 356/432 |
| 5,404,755 A | 4/1995 | Olson et al. | |
| 5,554,808 A * | 9/1996 | Chiao | G01N 29/07 |
| | | | 73/598 |
| 5,556,764 A * | 9/1996 | Sizto | G06K 9/00127 |
| | | | 382/133 |
| 5,619,587 A | 4/1997 | Willoughby, Jr. et al. | |
| 6,234,025 B1 * | 5/2001 | Gieske | G01N 29/221 |
| | | | 73/629 |
| 6,637,266 B1 | 10/2003 | Froom | |
| 6,856,918 B2 | 2/2005 | Dubois et al. | |
| 7,467,052 B2 | 12/2008 | Vaccaro | |
| 7,584,062 B1 | 9/2009 | Tat et al. | |
| 7,822,258 B2 | 10/2010 | Senibi et al. | |
| 8,332,165 B1 | 12/2012 | Tat et al. | |
| 2002/0141632 A1 | 10/2002 | Engelbart et al. | |
| 2003/0154801 A1 | 8/2003 | Georgeson | |
| 2004/0031337 A1 | 2/2004 | Masaniello et al. | |
| 2005/0047643 A1 * | 3/2005 | Lowe | G01N 21/8851 |
| | | | 382/141 |
| 2005/0102109 A1 | 5/2005 | Dubois et al. | |
| 2005/0241397 A1 | 11/2005 | Bergman | |
| 2007/0165918 A1 * | 7/2007 | Howard | G01N 29/07 |
| | | | 382/128 |
| 2009/0148030 A1 | 6/2009 | Engelbart et al. | |
| 2010/0126277 A1 | 5/2010 | Wu et al. | |
| 2010/0329081 A1 | 12/2010 | Sullivan et al. | |
| 2012/0250970 A1 * | 10/2012 | Tsubaki | G01N 29/0654 |
| | | | 382/131 |

OTHER PUBLICATIONS

Smith, R. A., et al.; Automated Non-Destructive Analysis and Advanced 3D Defect Characterisation From Ultrasonic Scans of Composites; Presented at the 17th International Conference on Composite Materials; Jul. 27, 2009; Edinburgh.

UTSIM—Center for Nondestructive Evaluation; http://www.cnde.iastate.edu/ultrasonics/utsim; Copyright 2011 Center for NDE Iowa State University; 3 pages.

Image3D Ultrasonic Simulation; UTEX Scientific; http://www.utex.com; retrieved Jan. 20, 2012; 1 page.

CIVA: State of the Art Simulation Software for Non Destructive Testing; http://www-cive.cea.fr; © CEA 2003-2012; 2 pages.

About PZFlex; http://www.pzflex.com; © 2011 Weidlinger Associates; 2 pages.

U.S. Appl. No. 13/355,100, filed Jan. 20, 2012.

International Search Report and Written Opinion of International Application No. PCT/US2014/034661; Jul. 3, 2014; 12 pages.

Thomas, M. et al.; Representative Volume Element of Anisotropic Carbon-Epoxy Composite with High-Fibre Volume Fraction; Composites Science and Technology; Dec. 1, 2008; pp. 3184-3192; vol. 68, No. 15-16.

Frock, B. et al.; Applications of Digital Image Enhancement Techniques to the Ultrasonic NDE Composite Materials; Acoustical Imaging; Jul. 14, 1986; pp. 461-469; vol. 15.

Djukic, L. et al.; Contrast Enhancement in Visualisation of Woven Composite Tow Architecture Using a MicroCT Scanner, Part 1; Fabric Coating and Resin Additives; Composites: Part A; May 1, 2009; pp. 553-565; vol. 40, No. 5.

U.S. Appl. No. 12/861,076, filed Aug. 23, 2010.

* cited by examiner

METHODS AND SYSTEMS FOR INSPECTION OF COMPOSITE IRREGULARITIES

BACKGROUND

The present disclosure relates generally to nondestructive evaluation of materials and, more particularly, to methods and systems for use in inspecting a composite structure for irregularities.

Known aircraft systems are increasingly being fabricated from composite materials. At least some structures fabricated from composite materials may undergo nondestructive evaluation and/or inspection prior to installation and/or use to ensure that irregularities, such as wrinkles, have not formed during fabrication that may affect and/or alter a mechanical property of the composite material.

One known method of inspecting such structures includes pulse-echo ultrasound and/or X-ray radiography. At least some such methods, however, include human analysis of ultrasound or X-ray images to determine the presence of an irregularity and, thus, a human error element is introduced. Moreover, at least some such methods may be tedious and/or time consuming.

BRIEF SUMMARY

In one aspect, a method is provided for use in inspecting a composite structure. The method includes acquiring an image of the composite structure. The composite structure includes at least a first ply and a second ply adjacent the first ply. The method also includes transforming the image into a binary image, and determining a first boundary line between the first ply and the second ply. The method further includes characterizing an irregularity in the composite structure based at least partially on the first boundary line.

In another aspect, a computer-readable storage device is provided having encoded thereon computer readable instructions that are executable by a processor to perform functions including acquiring an image of a composite structure. The composite structure includes at least a first ply and a second ply adjacent the first ply. The instructions are executable by the processor to perform functions further including transforming the image into a binary image, and determining a first boundary line between the first ply and the second ply. The instructions are executable by the processor to perform functions further including characterizing an irregularity in the composite structure based at least partially on the first boundary line In yet another aspect, a system is provided. The system includes a scanning module configured to acquire an image of a composite structure. The composite structure includes at least a first ply and a second ply adjacent the first ply. The system further includes a binary imaging module configured to transform the image into a binary image, and an evaluating module configured to determine a first boundary line between the first ply and the second ply, and characterize an irregularity in the composite structure based at least partially on the first boundary line.

DETAILED DESCRIPTION

Figure 1:
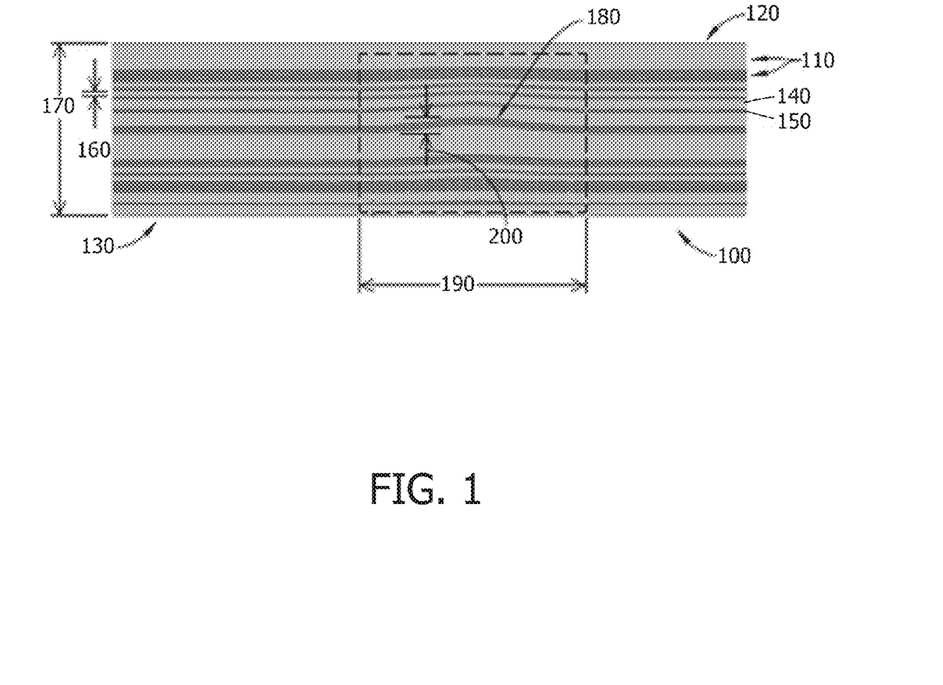
FIG. 1 is a cross-sectional view of a coupon of an exemplary composite structure.

FIG. 1 is a cross-sectional view of a portion or coupon of an exemplary composite structure 100. In the exemplary implementation, composite structure 100 includes a plurality of plies 110, a top surface 120, and a bottom surface 130. In the exemplary implementation, each ply 110 includes a plurality of carbon fibers embedded in a polymer matrix. More specifically, in the exemplary implementation, plies 110 include at least a first ply 140 including fibers arranged in a first direction, and a second ply 150 including fibers arranged in a second orientation different from the first direction. In one implementation, the first orientation is substantially perpendicular to the second orientation. Alternatively, fibers of each ply 110 may be arranged in any orientation that enables the methods and systems to function as described herein.

In the exemplary implementation, composite structure 100 has at least one composite structure parameter including a ply thickness, a number of plies, a ply layup, a composite structure thickness, and/or a material used to fabricate at least a portion of the at least one composite structure. For example, in the exemplary implementation, each ply 110 has a thickness 160, and composite structure 100 has a total thickness 170 extending between top surface 120 and bottom surface 130.

A portion of composite structure 100 includes an irregularity 180 between surfaces 120 and 130. That is, in the exemplary implementation, plies 110 are not substantially uniform along a length 190 or width of irregularity 180. In the exemplary implementation, irregularity 180 is positioned entirely within composite structure 100, such that a degree of irregularity 180 (e.g., irregularity height 200) is generally reduced near top surface 120 and/or a bottom surface 130 of composite structure 100. That is, in the exemplary implementation, irregularity 180 is not visible and/or less visible by the naked eye near top surface 120 and/or bottom surface 130. In the exemplary implementation, irregularity 180 is a composite wrinkle and/or a ply distortion.

Figure 2:
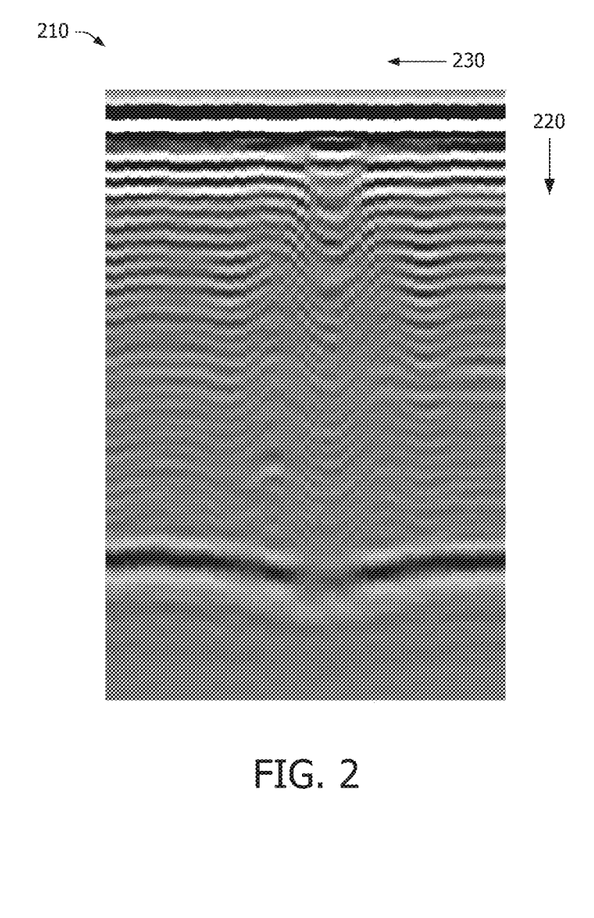
FIG. 2 is an exemplary cross-sectional representation of the composite structure shown in FIG. 1.

FIG. 2 is a cross-sectional representation of composite structure 100 that shows a depth of composite structure 100 along the Y-axis and a length or width of composite structure 100 along the X-axis. Alternatively, the cross-sectional representation may be oriented in any direction that enables the methods and systems to function as described herein.

In the exemplary implementation, the cross-sectional representation is a first brightness scan (B-scan) image 210 including a plurality of amplitude modulation scans (A-scans) in grayscale, wherein each pixel of B-scan image 210 represents intensity information (e.g., the amplitude, magnitude, and/or intensity of the echo signal) associated with the respective A-scan. In the exemplary implementation, each A-scan is generated by transmitting an ultrasonic wave through composite structure 100 in a first direction 220 (e.g., traversing a depth of composite structure 100), and plotting an amplitude, magnitude, and/or intensity of an echo signal associated with the ultrasonic wave. In the exemplary implementation, B-scan is image 210 is generated by plotting an A-scan for each point in a plurality of points extending along a second direction 230 substantially perpendicular to first direction 220 (e.g., a length or width of composite structure 100). Accordingly, in the exemplary implementation, B-scan image 210 includes a plurality of vertical lines, wherein each vertical line is associated with a respective A-scan. Alternatively, the cross-sectional representation may be generated and/or acquired using any device and/or method that enables the methods and systems to function as described herein, such as, without limitation, taking a photomicrograph or using a destructive method (e.g., taking a test portion or coupon) of composite structure 100.

Figure 3:
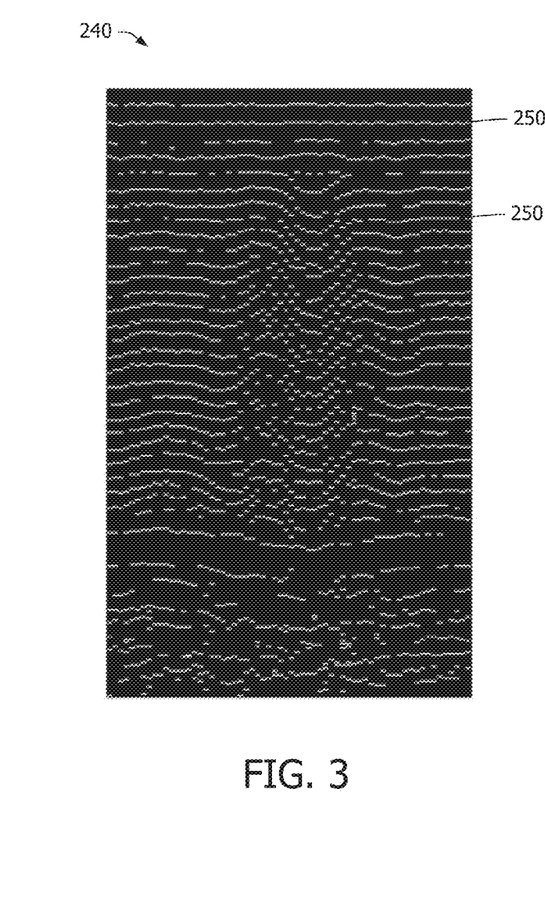
FIG. 3 is an exemplary binary image of the composite structure shown in FIG. 1.

FIG. 3 is a first binary image 240 that shows the data associated with B-scan image 210 (shown in FIG. 2) in a simplified format. For example, in the exemplary implementation, the grayscale B-scan image 210 has a first plurality of intensities or values (e.g., 256 values of grayscale), and binary image 240 has a second plurality of intensities or values that is fewer than the first plurality of values (e.g., 2 values: black and white). In the exemplary implementation, binary image 240 is generated by plotting at least the peaks and/or valleys of the A-scans in B-scan image 210. More specifically, in the exemplary implementation, a peak or a valley of an A-scan is represented by a first or white point 250 (e.g., "one") on binary image 240 while all other values are represented by a second point or no point at all (e.g., "zero"). Accordingly, in such an implementation, white point 250 represents a potential irregularity, and the second point represents a negligible or permissible irregularity or no irregularity.

Figure 4:
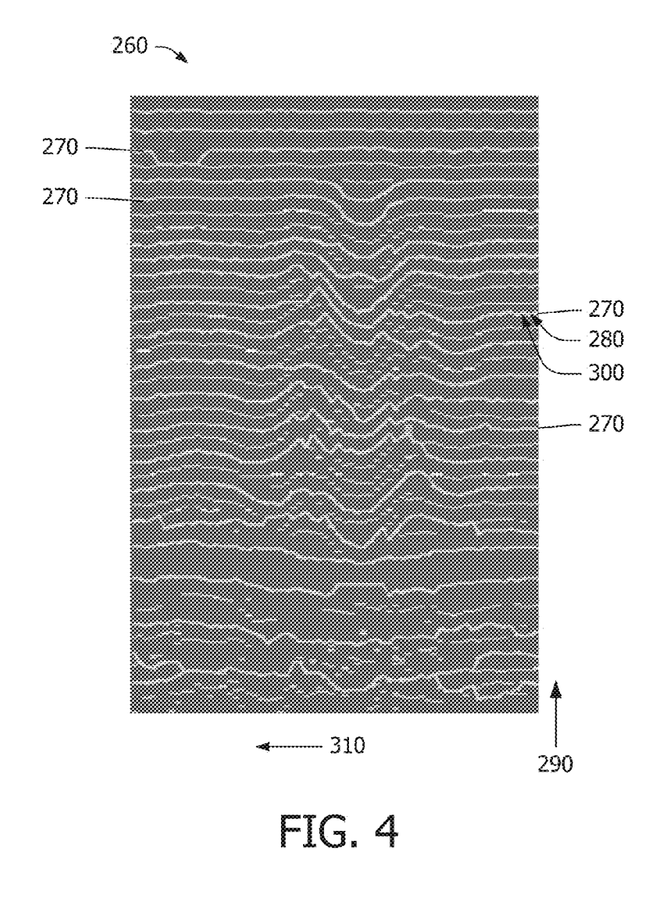
FIG. 4 shows the binary image shown in FIG. 3 with a plurality of boundary lines plotted on the binary image.

FIG. 4 is a second binary image 260 that includes first binary image 240 (shown in FIG. 3) and a plurality of boundary lines 270 plotted on first binary image 240. In the exemplary implementation, boundary lines 270 are plotted based on positions of white points 250 and rules specified in an algorithm. For example, in the exemplary implementation, boundary line 270 extends between a first white point 280 on a first side 290 (e.g., a right side) of binary image 260 and at least one second white point 300 horizontally downstream 310 (e.g., to the left) of first white point 280 based on rules specified in an algorithm. In the exemplary implementation, second white point 300 is identified based on a variety of different rules and/or factors including, without limitation, a proximity of first and second white points 280 and 300, a difference in a vertical position of first and second white points 280 and 300, a difference in a horizontal position of first and second white points 280 and 300, and/or a shape of an adjacent and/or previously plotted boundary line 270. In the exemplary implementation, a boundary line 270 is plotted at an estimated interface between plies 110.

Boundary lines 270 may be plotted in any position and/or orientation that enables the methods and systems to function as described herein. In one implementation, a boundary line 270 may be plotted between first and second white points 280 and 300 where a determined proximity and/or difference satisfies (e.g., is less than) a predetermined threshold. Accordingly, in such an implementation, more weight and/or additional consideration may be given to a second white point 300 that is closer to first white point 280 than a second white point 300 that is further from first white point 280. Additionally or alternatively, more weight and/or additional consideration may be given to a second white point 300 that results in a boundary line 270 following a pattern that is substantially similar and/or the same as that of an adjacent boundary line 270 than a second white point 300 that results in a boundary line 270 that does not follow a pattern that is substantially similar and/or the same as that of an adjacent boundary line 270.

Figure 5:
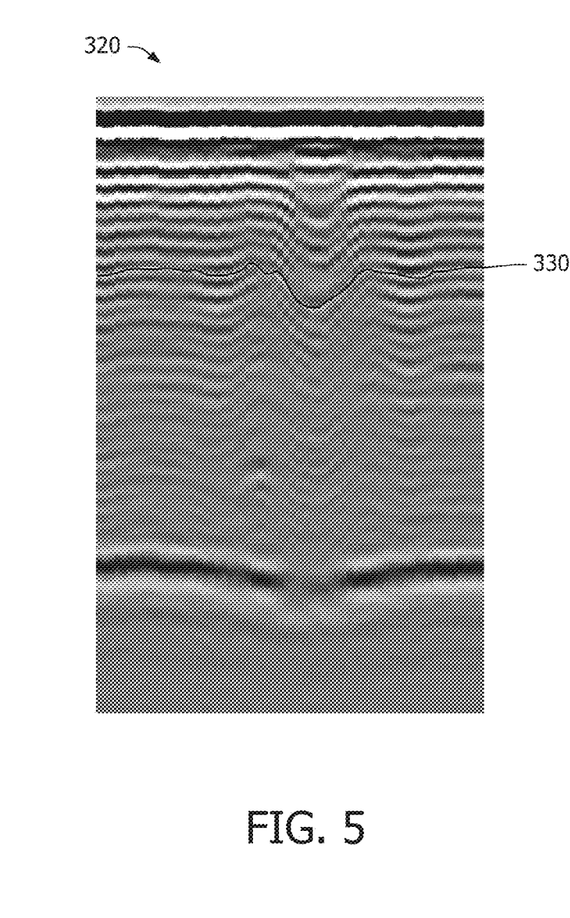
FIG. 5 shows the cross-sectional representation shown in FIG. 2 with a characterized irregularity.

FIG. 5 is a second B-scan image 320 that includes first B-scan image 210 (shown in FIG. 2) and at least one irregularity 330 plotted on first B-scan image 320. Accordingly, in the exemplary implementation irregularity 330 characterizes and/or is a virtual representation of a corresponding irregularity 180 in composite structure 100 (shown in FIG. 1). In the exemplary implementation, irregularities 330 are plotted based on at least one boundary line 270 and rules specified in an algorithm. In the exemplary implementation, each boundary line 270 that satisfies (e.g., is greater than) a predetermined threshold is plotted as an irregularity 330. For example, in one implementation, a vertical height is determined for each boundary line 270 by calculating a difference between a minimum vertical location (i.e., a valley) and a maximum vertical location (i.e., a peak), and each boundary line 270 having a vertical height that satisfies the predetermined threshold is plotted as irregularity 330. In some implementations, the predetermined threshold may be a relative threshold such that a predetermined number of irregularities 330 are plotted (e.g., the one largest irregularity). Alternatively, the predetermined threshold may be an absolute threshold such that each plotted irregularity 330 has a vertical height that is greater than (or equal to) a predetermined height.

Figure 6:
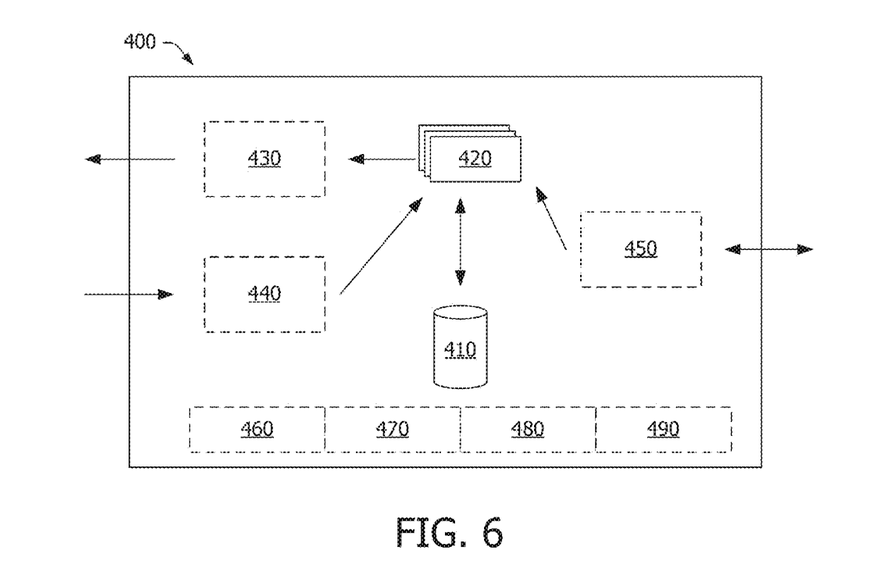
FIG. 6 is a schematic illustration of an exemplary computer system that may be used to inspect the composite structure shown in FIG. 1 and/or characterize the irregularity shown in FIG. 5.

FIG. 6 is a schematic illustration of an exemplary computer system 400 that may be used to inspect composite structure 100 and/or characterize irregularity 180. In the exemplary implementation, computer system 400 includes a memory device 410 and a processor 420 coupled to memory device 410 for use in executing instructions. More specifically, in the exemplary implementation, computer system 400 is configurable to perform one or more operations described herein by programming memory device 410 and/or processor 420. For example, processor 420 may be programmed by encoding an operation as one or more executable instructions and by providing the executable instructions in memory device 410.

Processor 420 may include one or more processing units (e.g., in a multi-core configuration). As used herein, the term "processor" is not limited to integrated circuits referred to in the art as a computer, but rather broadly refers to a controller, a microcontroller, a microcomputer, a programmable logic controller (PLC), an application specific integrated circuit, and other programmable circuits.

In the exemplary implementation, memory device 410 includes one or more devices (not shown) that enable information such as executable instructions and/or other data to be selectively stored and retrieved. In the exemplary implementation, such data may include, but is not limited to, properties of composite materials, properties of ultrasonic waves, imaging data, calibration curves, operational data, and/or control algorithms. Alternatively, computer system 400 may use any algorithm and/or method that enables the methods and systems to function as described herein. Memory device 410 may also include one or more computer readable media, such as, without limitation, dynamic random access memory (DRAM), static random access memory (SRAM), a solid state disk, and/or a hard disk.

In the exemplary implementation, computer system 400 includes a presentation interface 430 that is coupled to processor 420 for use in presenting information to a user. For example, presentation interface 430 may include a display adapter (not shown) that may couple to a display device (not shown), such as, without limitation, a cathode ray tube (CRT), a liquid crystal display (LCD), a light-emitting diode (LED) display, an organic LED (OLED) display, an "electronic ink" display, and/or a printer. In some implementations, presentation interface 430 includes one or more display devices.

Computer system 400, in the exemplary implementation, includes an input interface 440 for receiving input from the user. For example, in the exemplary implementation, input interface 440 receives information suitable for use with the methods described herein. Input interface 440 is coupled to processor 420 and may include, for example, a joystick, a keyboard, a pointing device, a mouse, a stylus, a touch sensitive panel (e.g., a touch pad or a touch screen), and/or a position detector. It should be noted that a single component, for example, a touch screen, may function as both presentation interface 430 and as input interface 440.

In the exemplary implementation, computer system 400 includes a communication interface 450 that is coupled to processor 420. In the exemplary implementation, communication interface 450 communicates with at least one remote device. For example, communication interface 450 may use, without limitation, a wired network adapter, a wireless network adapter, and/or a mobile telecommunications adapter. A network (not shown) used to couple computer system 400 to the remote device may include, without limitation, the Internet, a local area network (LAN), a wide area network (WAN), a wireless LAN (WLAN), a mesh network, and/or a virtual private network (VPN) or other suitable communication means.

In the exemplary implementation, computer system 400 includes at least a scanning module 460, an ultrasonic imaging module 470, a binary imaging module 480, and an evaluating module 490 that enable the methods and systems to function as described herein. Modules 460, 470, 480, and/or 490 may be in the form of any combination of software and/or hardware.

Figure 7:
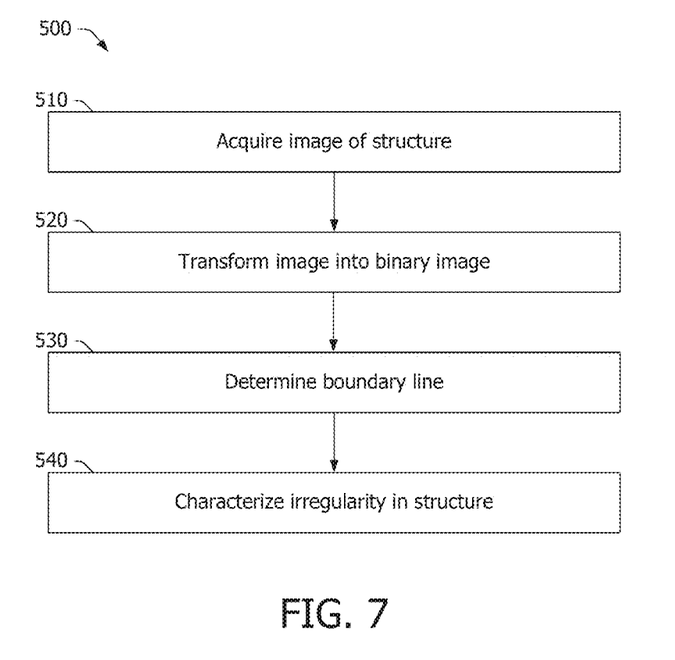
FIG. 7 is a flowchart of an exemplary method that may be implemented by the computer system shown in FIG. 6 to inspect the composite structure shown in FIG. 1 and/or characterize the irregularity shown in FIG. 5.

FIG. 7 is a flowchart of an exemplary method 500 that may be implemented by computer system 400. In the exemplary implementation, scanning module 460 includes and/or is coupled to a transducer that transmits ultrasound waves towards composite structure 100. The ultrasound waves reflect off of plies 110 and/or the interfaces between adjacent plies 110 and produce echo signals that are reflected back towards the transducer. In the exemplary implementation, scanning module 460 detects the echo signals and produces relative time-domain electrical signals. In the exemplary implementation, ultrasonic imaging module 470 generates a digital image based on the electrical signals and stores the signals as echo data in memory device 410. Alternatively, the image may be acquired and/or generated using any device and/or method that enables the methods and systems to function as described herein.

In the exemplary implementation, binary imaging module 480 receives and/or acquires 510 the image of composite structure 100 and transforms 520 the image into a binary image. In at least some implementations, the image may be preprocessed to facilitate transforming 520 the image into the binary image. For example, in one implementation, the image is filtered and/or thresholded to facilitate reducing noise in the image and/or increasing a visibility of a boundary line 270 between plies 110. In the exemplary implementation, evaluating module 490 determines 530 a boundary line 270 between first ply 140 and second ply 150, and characterizes 540 an irregularity 180 in composite structure 100 based at least partially on boundary line 270.

Figure 8:
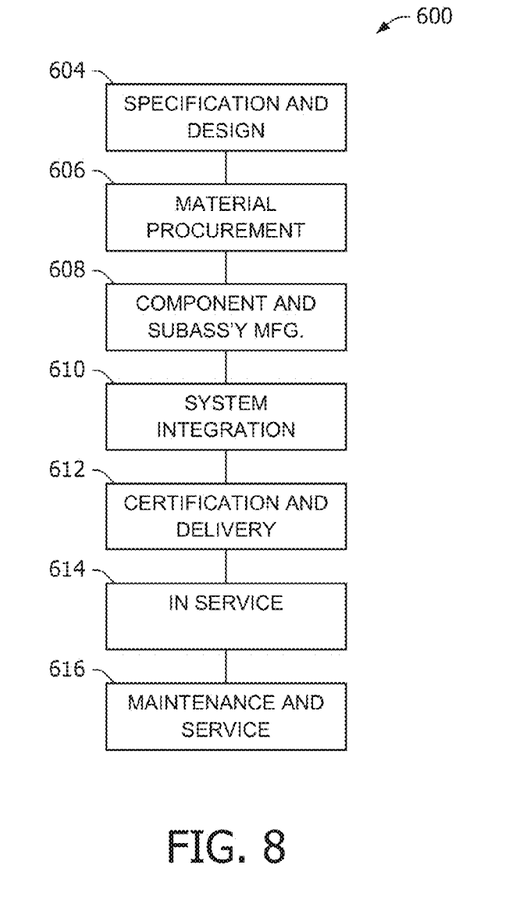
FIG. 8 is a flow diagram of aircraft production and service methodology.
Figure 9:
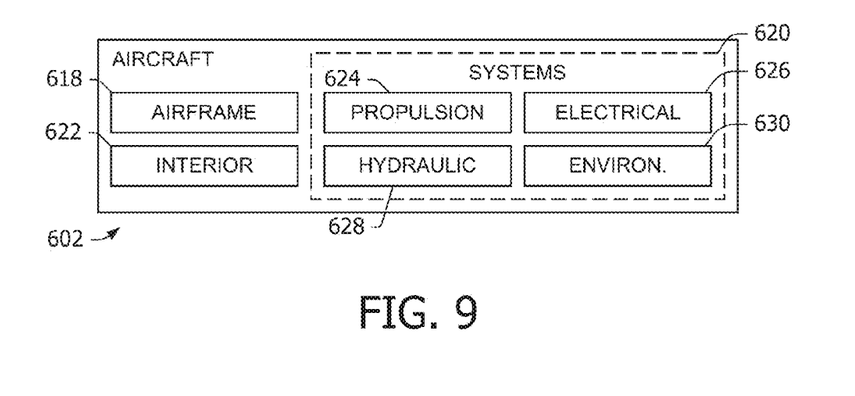
FIG. 9 is a block diagram of an aircraft that may be fabricated from the composite structure shown in FIG. 1.

The methods and systems described herein are in the context of an aircraft manufacturing and service method 600 as shown in FIG. 8 and an aircraft 602 as shown in FIG. 9. Alternatively, the methods and systems described herein may be implemented in any context and/or in any environment that enables the methods and systems to function as described herein. During pre-production, exemplary method 600 may include specification and design 604 of the aircraft 602 and material procurement 606. During production, component and subassembly manufacturing 608 and system integration 610 of the aircraft 602 takes place. Thereafter, the aircraft 602 may go through certification and delivery 612 in order to be placed in service 614. While in service by a customer, the aircraft 602 is scheduled for routine maintenance and service 616 (which may also include modification, reconfiguration, refurbishment, and so on).

Each of the processes of method 600 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 9, the aircraft 602 produced by exemplary method 600 may include an airframe 618 with a plurality of systems 620 and an interior 622. Examples of high-level systems 620 include one or more of a propulsion system 624, an electrical system 626, a hydraulic system 626, and an environmental system 130. Any number of other systems may be included. Although an aerospace example is shown, the principles of the invention may be applied to other industries, such as the automotive industry.

Apparatus and methods embodied herein may be employed during any one or more of the stages of the production and service method 600. For example, components or subassemblies corresponding to production process 608 may be fabricated or manufactured in a manner similar to components or subassemblies produced while the aircraft 602 is in service. Also, one or more apparatus implementations, method implementations, or a combination thereof may be utilized during the production stages 608 and 610, for example, by substantially expediting assembly of or reducing the cost of an aircraft 602. Similarly, one or more of apparatus implementations, method implementations, or a combination thereof may be utilized while the aircraft 602 is in service, for example and without limitation, to maintenance and service 616.

The implementations described herein relate generally to nondestructive evaluation of materials and, more particularly, to methods and systems for use in determining dimensions of a composite wrinkle or ply distortion in a composite structure. Exemplary implementations of methods and systems for inspecting composite structures for irregularities are described above in detail. The methods and systems are not limited to the specific implementations described herein, but rather, components of systems and/or steps of the method may be utilized independently and separately from other components and/or steps described herein. Each method step and each component may also be used in combination with other method steps and/or components. Although specific features of various implementations may be shown in some drawings and not in others, this is for convenience only. Any feature of a drawing may be referenced and/or claimed in combination with any feature of any other drawing.

An element or step recited in the singular and proceeded with the word "a" or "an" should be understood as not excluding plural elements or steps unless such exclusion is explicitly recited. Moreover, references to "one implementation" of the present invention and/or the "exemplary implementation" are not intended to be interpreted as excluding the existence of additional implementations that also incorporate the recited features.

Implementations of the systems and methods described herein may embrace one or more computer-readable media, wherein each medium may be configured to include or includes thereon data or computer-executable instructions for manipulating data. The computer-executable instructions include data structures, objects, programs, routines, or other program modules that may be accessed by a processing system, such as one associated with a general-purpose computer capable of performing various different functions or one associated with a special-purpose computer capable of performing a limited number of functions. Computer-executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer-readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system.

The methods described herein may be encoded as executable instructions embodied in a computer readable medium, including, without limitation, a storage device or a memory area of a computing device. Such instructions, when executed by one or more processors, cause the processor(s) to perform at least a portion of the methods described herein. As used herein, a "storage device" is a tangible article, such as a hard drive, a solid state memory device, and/or an optical disk that is operable to store data, such as computer-executable instructions.

This written description uses examples to disclose the implementations, including the best mode, and also to enable any person skilled in the art to practice the implementations, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of inspecting a composite structure, said method comprising:

acquiring an ultrasound B-scan cross-sectional image of a depth of the composite structure, wherein the depth of the composite structure is defined by at least a first ply and a second ply laid up on the first ply, the cross-sectional ultrasound B-scan image representing intensity information of a plurality of A-scan ultrasound waves plotted in grayscale;

transforming the acquired ultrasound B-scan cross-sectional image into a binary image;

determining a first boundary line between the first ply and the second ply based at least partially on a position of each of a plurality of data points plotted in the binary image;

calculating a vertical height as a difference between a minimum vertical location and a maximum vertical location of the first boundary line determined in the binary image;

characterizing, based on the binary image, presence of a wrinkle and associated wrinkle height relative to the depth of the composite structure acquired from the binary image of the ultrasound B-scan cross-sectional image, wherein the wrinkle is characterized when the calculated vertical height of the first boundary line determined in the binary image is greater than a predetermined threshold; and displaying a virtual representation of the characterized wrinkle on the acquired binary image of the ultrasound B-scan cross-sectional image.

2. A method in accordance with claim 1, wherein acquiring the cross-sectional image comprises acquiring a photomicrograph of the cross-section of the composite structure.

3. A method in accordance with claim 1 further comprising determining a shape of the first boundary line, and determining a second boundary line based at least partially on the shape of the first boundary line.

4. A computer-readable storage device having encoded thereon computer readable instructions that are executable by a processor to perform functions comprising:

acquiring an ultrasound B-scan cross-sectional image of a depth of a composite structure, wherein the depth of the composite structure is defined by at least a first ply and a second ply laid up on the first ply, the cross-sectional ultrasound B-scan image representing intensity information of a plurality of A-scan ultrasound waves plotted in grayscale;

transforming the acquired ultrasound B-scan cross-sectional image into a binary image;

determining a first boundary line between the first ply and the second ply based at least partially on a position of each of a plurality of data points plotted in the binary image;

calculating a vertical height as a difference between a minimum vertical location and a maximum vertical location of the first boundary line determined in the binary image;

characterizing, based on the binary imam presence of a wrinkle and associated wrinkle height relative to the depth of the composite structure acquired from the binary image of the ultrasound B-scan cross-sectional image, wherein the wrinkle is characterized when the calculated vertical height of the first boundary line determined in the binary image is greater than a predetermined threshold; and displaying a virtual representation of the characterized wrinkle on the acquired binary image of the ultrasound B-scan cross-sectional image.

5. A computer-readable storage device in accordance with claim 4, wherein the instructions are executable by the processor to perform functions comprising acquiring a photomicrograph of the cross-section of the composite structure.

6. A computer-readable storage device in accordance with claim 4, wherein the instructions are executable by the processor to perform functions comprising determining a shape of the first boundary line, and determining a second boundary line based at least partially on the shape of the first boundary line.

7. A system comprising:
- a scanning module configured to acquire an ultrasound B-scan cross-sectional image of a depth of a composite structure, wherein the depth of the composite structure is defined by at least a first ply and a second ply laid up on the first ply, the cross-sectional ultrasound B-scan image representing intensity information of a plurality of A-scan ultrasound waves plotted in grayscale;
- a binary imaging module configured to transform the acquired ultrasound B-scan cross-sectional image into a binary image; and
- an evaluating module configured to determine a first boundary line between the first ply and the second ply based at least partially on a position of each of a plurality of data points plotted in the binary image, calculate a vertical height as a difference between a minimum vertical location and a maximum vertical location of the first boundary line determined in the binary image, characterize, based on the binary image, presence of a wrinkle and associated wrinkle height relative to the depth of the composite structure acquired from the binary image of the ultrasound B-scan cross-sectional image, wherein the wrinkle is characterized when the calculated vertical height of the first boundary line determined in the binary image is greater than a predetermined threshold, and display a virtual representation of the characterized wrinkle on the acquired binary image of the ultrasound B-scan cross-sectional image.

8. A system in accordance with claim 7, wherein the scanning module is configured to acquire a photomicrograph of the cross-section of the composite structure.

9. A system in accordance with claim 7, wherein the evaluating module is configured to determine a shape of the first boundary line, and determine a second boundary line based at least partially on the shape of the first boundary line.

* * * * *

UNITED STATES PATENT AND TRADEMARK OFFICE
CERTIFICATE OF CORRECTION

PATENT NO. : 9,595,092 B2  
APPLICATION NO. : 13/891688  
DATED : March 14, 2017  
INVENTOR(S) : Wu et al.

Page 1 of 1

It is certified that error appears in the above-identified patent and that said Letters Patent is hereby corrected as shown below:

In the Claims

In Column 8, Line 57, Claim 4, delete "imam" and insert therefor -- image, --.

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*